(12) United States Patent
Garcia Garcia et al.

(10) Patent No.: US 11,241,032 B2
(45) Date of Patent: Feb. 8, 2022

(54) AEROSOL GENERATING ARTICLES AND METHODS FOR MANUFACTURING THE SAME

(71) Applicant: JT International S.A., Geneva (CH)

(72) Inventors: Eduardo José Garcia Garcia, Grand-Sacconex (CH); Andrew Rogan, Forres (GB); Takashi Hasegawa, Tokyo (JP); Peter Uhrmeister, Trier (DE)

(73) Assignee: JT International S.A.

( * ) Notice: Subject to any disclaimer, the term of this patent is extended or adjusted under 35 U.S.C. 154(b) by 0 days.

(21) Appl. No.: 16/768,382

(22) PCT Filed: Dec. 21, 2018

(86) PCT No.: PCT/EP2018/086528
§ 371 (c)(1),
(2) Date: May 29, 2020

(87) PCT Pub. No.: WO2019/129694
PCT Pub. Date: Jul. 4, 2019

(65) Prior Publication Data
US 2020/0359676 A1     Nov. 19, 2020

(30) Foreign Application Priority Data

Dec. 29, 2017  (EP) ..................................... 17211198
Jul. 26, 2018   (EP) ..................................... 18185843

(51) Int. Cl.
*A24B 3/00*      (2006.01)
*A24C 5/00*      (2020.01)
(Continued)

(52) U.S. Cl.
CPC .................. *A24B 3/14* (2013.01); *A24C 5/01* (2020.01); *A24D 1/20* (2020.01); *B32B 5/02* (2013.01);
(Continued)

(58) Field of Classification Search
CPC ....... B32B 2038/047; B29C 2793/0045; Y10T 156/1056; Y10T 156/1057
(Continued)

(56) References Cited

U.S. PATENT DOCUMENTS

2017/0055582 A1* 3/2017 Blandino ................. A24D 1/20
2018/0184713 A1* 7/2018 Mironov ................. A24F 40/30

FOREIGN PATENT DOCUMENTS

WO      2015177252 A1    11/2015
WO      2015177264 A1    11/2015
(Continued)

OTHER PUBLICATIONS

International Search Report from Application No. PCT/EP2018/086528 dated Apr. 12, 2019, 4 pages.
(Continued)

*Primary Examiner* — Linda L Gray
(74) *Attorney, Agent, or Firm* — Lerner, David, Littenberg, Krumholz & Mentlik, LLP (57) ABSTRACT

A sheet-type aerosol generating article includes at least two aerosol generating sheets each having aerosol generating material and an inductively heatable susceptor The inductively heatable susceptor is positioned between the aerosol generating sheets and each of the aerosol generating sheets has an exposed surface. Methods for manufacturing sheet-type aerosol generating articles are also disclosed.

18 Claims, 9 Drawing Sheets

(51) Int. Cl.
| | |
|---|---|
| A24D 1/00 | (2020.01) |
| B32B 5/00 | (2006.01) |
| B32B 7/00 | (2019.01) |
| B32B 15/00 | (2006.01) |
| B32B 29/00 | (2006.01) |
| B32B 37/00 | (2006.01) |
| B32B 38/00 | (2006.01) |
| A24B 3/14 | (2006.01) |
| A24C 5/01 | (2020.01) |
| A24D 1/20 | (2020.01) |
| B32B 5/02 | (2006.01) |
| B32B 5/16 | (2006.01) |
| B32B 5/18 | (2006.01) |
| B32B 7/12 | (2006.01) |
| B32B 15/04 | (2006.01) |
| B32B 15/14 | (2006.01) |
| B32B 15/16 | (2006.01) |
| B32B 15/18 | (2006.01) |
| B32B 15/20 | (2006.01) |
| B32B 29/02 | (2006.01) |
| B32B 29/04 | (2006.01) |
| B32B 37/12 | (2006.01) |
| B32B 37/20 | (2006.01) |
| B32B 38/04 | (2006.01) |
| A24F 1/20 | (2006.01) |

(52) U.S. Cl.
CPC .............. *B32B 5/16* (2013.01); *B32B 5/18* (2013.01); *B32B 7/12* (2013.01); *B32B 15/04* (2013.01); *B32B 15/046* (2013.01); *B32B 15/14* (2013.01); *B32B 15/16* (2013.01); *B32B 15/18* (2013.01); *B32B 15/20* (2013.01); *B32B 29/002* (2013.01); *B32B 29/007* (2013.01); *B32B 29/02* (2013.01); *B32B 29/04* (2013.01); *B32B 37/12* (2013.01); *B32B 37/20* (2013.01); *B32B 38/0004* (2013.01); *B32B 38/04* (2013.01); *A24F 1/20* (2013.01); *B32B 2038/047* (2013.01); *B32B 2262/06* (2013.01); *B32B 2264/06* (2013.01); *B32B 2307/20* (2013.01); *B32B 2311/12* (2013.01); *B32B 2311/22* (2013.01); *B32B 2311/24* (2013.01); *B32B 2311/30* (2013.01); *B32B 2317/00* (2013.01); *B32B 2317/12* (2013.01)

(58) Field of Classification Search
USPC .................................................. 156/252, 253
See application file for complete search history.

(56) References Cited

FOREIGN PATENT DOCUMENTS

| WO | 2017005705 A1 | 1/2017 |
| WO | 2017068093 A1 | 4/2017 |
| WO | 2017178394 A1 | 10/2017 |

OTHER PUBLICATIONS

Extended European Search Report including Written Opinion for Application No. EP17211198.1, dated Jul. 6, 2018, pp. 1-9.
International Search Report including Written Opinion for Application No. PCT/EP2018/086525, dated Apr. 2, 2019, pp. 1-18.

* cited by examiner

AEROSOL GENERATING ARTICLES AND METHODS FOR MANUFACTURING THE SAME

CROSS-REFERENCE TO RELATED APPLICATIONS

The present application is a national phase entry under 35 U.S.C. § 371 of International Application No. PCT/EP2018/086528, filed Dec. 21, 2018, published in English, which claims priority to European Application No. 17211198.1 filed Dec. 29, 2017 and to European Application No. 18185843.2 filed Jul. 26, 2018, the disclosures of all of which are incorporated herein by reference.

TECHNICAL FIELD

The present disclosure relates to generally to aerosol generating articles, and more particularly to a sheet-type aerosol generating article for use with an aerosol generating device for heating the aerosol generating article to generate an aerosol for inhalation by a user. Embodiments of the present disclosure also relate to methods for manufacturing an aerosol generating article.

TECHNICAL BACKGROUND

Devices which heat, rather than burn, an aerosol generating material to produce an aerosol for inhalation have become popular with consumers in recent years.

Such devices can use one of a number of different approaches to provide heat to the aerosol generating material. One such approach is to provide an aerosol generating device which employs an induction heating system and into which an aerosol generating article, comprising aerosol generating material, can be removably inserted by a user. In such a device, an induction coil is provided with the device and an induction heatable susceptor is provided with the aerosol generating article. Electrical energy is provided to the induction coil when a user activates the device which in turn generates an alternating electromagnetic field. The susceptor couples with the electromagnetic field and generates heat which is transferred, for example by conduction, to the aerosol generating material and an aerosol is generated as the aerosol generating material is heated.

The characteristics of the aerosol generated by the aerosol generating device are dependent upon a number of factors, including the construction of the aerosol generating article used with the aerosol generating device. There is, therefore, a desire to provide an aerosol generating article which enables the characteristics of the aerosol generated during use of the article to be optimised and which is also easy to manufacture.

SUMMARY OF THE DISCLOSURE

According to a first aspect of the present disclosure, there is provided a sheet-type aerosol generating article comprising:
   at least two aerosol generating sheets each comprising aerosol generating material; and
   an inductively heatable susceptor;
   wherein the inductively heatable susceptor is positioned between the aerosol generating sheets and each of the aerosol generating sheets has an exposed surface.

According to a second aspect of the present disclosure, there is provided a method for manufacturing a sheet-type aerosol generating article comprising:
   (i) positioning an inductively heatable susceptor between two aerosol generating sheets each comprising aerosol generating material.

The aerosol generating article is for use with an aerosol generating device for heating the aerosol generating material, without burning the aerosol generating material, to volatise at least one component of the aerosol generating material and thereby generate an aerosol for inhalation by a user of the aerosol generating device.

The provision of an inductively heatable susceptor between the aerosol generating sheets provides for effective heat transfer from the inductively heatable susceptor to the aerosol generating material. This in turn provides for optimum heating of the aerosol generating material and ensures that the characteristics of the aerosol generated during use of the article are optimised. Effective transfer of the generated aerosol from the aerosol generating sheets is also assured due to the position of the aerosol generating sheets and the provision of exposed surfaces. The sheet-type construction of the aerosol generating article also facilitates manufacture of the article.

The aerosol generating sheets may be adhered to the inductively heatable susceptor. The aerosol generating sheets may be adhered to the inductively heatable susceptor by an adhesive which may be substantially non-electrically conductive and non-magnetically permeable. Adhering the aerosol generating sheets to the inductively heatable susceptor may facilitate manufacture of the aerosol generating article and ensure that it has the required structural integrity.

The aerosol generating sheets positioned on opposite sides of the inductively heatable susceptor may have different thicknesses. The aerosol generating sheets positioned on opposite sides of the inductively heatable susceptor may have the same thickness, with a greater number of the aerosol generating sheets being positioned on one side of the inductively heatable susceptor than on the other side of the inductively heatable susceptor and with the outermost aerosol generating sheet on each side of the inductively heatable susceptor having said exposed surface. With these arrangements, the sheet-type aerosol generating article can be used to produce a variety of final aerosol generating articles, for example of the stick-type. This could be achieved by cutting the sheet-type aerosol generating article to form a plurality of cut pieces and by positioning the cut pieces in a paper wrapper.

The inductively heatable susceptor may comprise a sheet of susceptor material which may separate the aerosol generating sheets. The use of a sheet of susceptor material may again facilitate manufacture of the aerosol generating article and ensure that it has the required structural integrity.

The thickness of the inductively heatable susceptor sheet may be less than the thickness of each of the aerosol generating sheets. For example, the thickness of the inductively heatable susceptor sheet may be less than half of the thickness of each of the aerosol generating sheets, and possibly less than one third of the thickness of each of the aerosol generating sheets. This may allow an aerosol to be generated more effectively during use of the aerosol generating article in an aerosol generating device and may allow the edge regions of the aerosol generating sheets to be deformed to cover the edge regions of the inductively heatable susceptor sheet (discussed further below).

The aerosol generating article may include perforations which extend through the article. In embodiments in which the inductively heatable susceptor comprises a sheet of susceptor material, the aerosol generating sheets and the inductively heatable susceptor sheet positioned therebetween may include perforations which extend through the sheets. The perforations advantageously facilitate air flow through the aerosol generating article during use in an aerosol generating device and may advantageously improve heating efficiency due to the skin effect. The perforations allow the porosity, and hence the air permeability, of the resultant aerosol generating article to be carefully controlled and optimised. For example, the aerosol generating article may have an air permeability of about 50 to about 20,000 CORESTA Units (CU)±10%.

An edge region of the inductively heatable susceptor sheet may be covered by a stretched or deformed edge region of at least one of the aerosol generating sheets. This may provide a number of advantages which are discussed later in this specification.

The inductively heatable susceptor may comprise a plurality of strips of susceptor material. The inductively heatable susceptor may comprise a particulate susceptor material. The use of susceptor strips or particulate susceptor material may facilitate manufacture of the aerosol generating article.

The aerosol generating article may comprise a further layer or sheet covering each of the aerosol generating sheets. The further layer or sheet may comprise a material which differs from the aerosol generating material and the inductively heatable susceptor material. Such an arrangement may facilitate handling of the aerosol generating article by a user. The further layer or sheet may comprise a material which is substantially non-electrically conductive and non-magnetically permeable, for example paper. Thus, the further layer or sheet is not inductively heated in the presence of a time varying electromagnetic field during use of the article with an aerosol generating device.

The further layer or sheet may be air-permeable. Effective transfer of the generated aerosol from the aerosol generating sheets is thereby assured.

The aerosol generating sheets may be adhered to each other by an adhesive. The aerosol generating article may comprise a layer of said adhesive between the aerosol generating sheets and the inductively heatable susceptor may be provided in the adhesive layer. The adhesive may be substantially non-electrically conductive and non-magnetically permeable. The inductively heatable susceptor may be distributed in the adhesive layer and may, for example, be distributed substantially uniformly in the adhesive layer or according to a predetermined pattern. This arrangement provides a robust structure with good structural integrity due to the adhesion of the aerosol generating sheets to each other. This arrangement is also easy to manufacture.

The inductively heatable susceptor may comprise one or more, but not limited, of aluminium, iron, nickel, stainless steel and alloys thereof, e.g. Nickel Chromium or Nickel Copper. With the application of an electromagnetic field in its vicinity, the susceptor may generate heat due to eddy currents and magnetic hysteresis losses resulting in a conversion of energy from electromagnetic to heat.

The inductively heatable susceptor may comprise a dotation of a ferromagnetic material. The ferromagnetic dotation advantageously increases heat generation, and hence heating efficiency, of the inductively heatable susceptor and may prevent overheating of the aerosol generating sheets. The inductively heatable susceptor may comprise a metal foil (e.g. an aluminium foil) with a dotation of a ferromagnetic material. By way of example, the ferromagnetic material may comprise iron, nickel, iron oxides, cobalt and alloys thereof. The ferromagnetic material may be selected based on its Curie temperature to match the intended purpose, for example to maximise heating efficiency (for which a higher Curie temperature may be preferred) or to minimise overheating (for which a lower Curie temperature may be preferred). For example, where the intention is to maximise heating efficiency, iron could be a straightforward choice for the ferromagnetic material with its Curie temperature of approximately 1000 K. Iron oxides or a set of alloys may also be a suitable choice. Cobalt could also be a possible choice for the ferromagnetic material because of its high Curie temperature of approximately 1400 K. Where the intention is to minimise overheating of the aerosol generating sheets, nickel could be a beneficial choice for the ferromagnetic material because of its lower Curie temperature of approximately 630 K.

The aerosol generating material may be any type of solid or semi-solid material. Example types of aerosol generating solids include powder, granules, pellets, shreds, strands, porous material or foam material. The aerosol generating material may comprise plant derived material and in particular, may comprise tobacco. The aerosol generating sheets may, for example, comprise reconstituted tobacco sheets including tobacco and any one or more of cellulose fibres, tobacco stalk fibres and inorganic fillers such as $CaCO_3$.

The aerosol generating material may comprise an aerosol generating liquid. The aerosol generating liquid may be impregnated into or absorbed by the aerosol generating sheets. The aerosol generating sheets may comprise a liquid absorbent material, for example a fibrous material.

The aerosol generating material may comprise at least one aerosol-former. Examples of aerosol-formers include polyhydric alcohols and mixtures thereof such as glycerine or propylene glycol. Typically, the aerosol generating material may comprise an aerosol-former content of between approximately 5% and approximately 50% on a dry weight basis. In some embodiments, the aerosol generating material may comprise an aerosol-former content of approximately 15% on a dry weight basis.

Upon heating, the aerosol generating material may release volatile compounds. The volatile compounds may include nicotine or flavour compounds such as tobacco flavouring.

In a first embodiment of the method according to the second aspect, the aerosol generating sheets may be continuous sheets and the method may further comprise:
 (ii) cutting the continuous sheets with the susceptor positioned therebetween.

A plurality of aerosol generating articles can be easily manufactured by this method. Step (ii) may comprise cutting the continuous aerosol generating sheets with or without cutting the susceptor positioned therebetween.

The inductively heatable susceptor may be a continuous susceptor and step (ii) may comprise simultaneously cutting the continuous sheets and the continuous susceptor positioned therebetween. For example, the inductively heatable susceptor may comprise a continuous sheet of susceptor material, and step (ii) may comprise simultaneously cutting the continuous aerosol generating sheets and the continuous sheet of susceptor material.

The inductively heatable susceptor may comprise a plurality of strips of susceptor material or a particulate susceptor material and step (ii) may comprise cutting the continuous aerosol generating sheets without cutting the susceptor material positioned therebetween.

The cut sheets obtained by step (ii) can be subjected to further manufacturing processes, such as further cutting of the sheets, mixing of the cut sheets with aerosol generating sheets (without inductively heatable susceptor sheets) and supplying the mixture to a receptacle, e.g. a capsule, a paper tube or a shell.

In a second embodiment of the method according to the second aspect, the aerosol generating sheets may be continuous sheets and the method may further comprise:

(ii) winding the continuous sheets with the susceptor positioned therebetween on a bobbin.

The resultant continuous sandwich of sheets wound on the bobbin can be supplied to a user for subsequent cutting to form aerosol generating articles of a desired size and/or for other processing operations. The resultant continuous sandwich of sheets wound on the bobbin can also be subjected to further manufacturing processes, such as cutting the sandwich of sheets, mixing of the cut sheets with aerosol generating sheets (without inductively heatable susceptor sheets) and supplying the mixture to a receptacle, e.g. a capsule, a paper tube or a shell. The provision of a bobbinized final sandwich of sheets may also facilitate storage and transportation due to the compact nature of the wound sheets and the resultant higher density per given pack weight. The bobbinized final sandwich of sheets can also be easily wrapped, e.g. vacuum packed, for example to prevent or minimise flavour loss from the aerosol generating sheets.

Step (i) may comprise positioning the inductively heatable susceptor on a first one of said aerosol generating sheets and positioning the second one of said aerosol generating sheets on the susceptor. This may facilitate manufacture of the aerosol generating article.

Step (i) may comprise:
mixing the inductively heatable susceptor with an adhesive; and
positioning the mixture on a first one of said aerosol generating sheets.

The inductively heatable susceptor can be positioned on the aerosol generating sheet with relative ease as it is contained within the mixture. This method of application may be particularly suitable when the inductively heatable susceptor is very small, for example in particulate form.

Step (i) may comprise:
positioning an adhesive on a first one of said aerosol generating sheets; and
positioning the inductively heatable susceptor on the adhesive.

The positioning of the inductively heatable susceptor on the aerosol generating sheet can be carefully controlled with this method of application because it is positioned separately from the adhesive.

The method may further comprise pressing the aerosol generating sheets and the inductively heatable susceptor positioned therebetween to thereby bond the aerosol generating sheets. The use of an adhesive may not be needed with this method, thereby simplifying the construction of the aerosol generating article and reducing the cost of manufacture.

The inductively heatable susceptor may be a continuous susceptor and may, for example, comprise a sheet of susceptor material. Step (i) may comprise positioning an aerosol generating sheet on a first surface of the continuous susceptor and may comprise positioning an aerosol generating sheet on a second surface of the continuous susceptor. Step (i) may comprise positioning the aerosol generating sheets on the first and second surfaces at the same position along the continuous susceptor. This simplifies the manufacturing process. In one example, step (i) may comprise pressing the aerosol generating sheets and the continuous susceptor to secure together the aerosol generating sheets and the continuous susceptor.

The step of pressing the aerosol generating sheets and the inductively heatable susceptor may comprise applying pressure to the aerosol generating sheets and the inductively heatable susceptor, for example using cooperating nip rollers. The application of local pressure to the aerosol generating sheets and the inductively heatable susceptor, for example by the nip rollers, ensures that they are reliably secured together.

The step of pressing the aerosol generating sheets and the inductively heatable susceptor may be performed at an elevated temperature. Performing the pressing at an elevated temperature may help to ensure that the aerosol generating sheets and the inductively heatable susceptor are reliably secured together.

The step of pressing the aerosol generating sheets and the inductively heatable susceptor may comprise embossing or debossing the aerosol generating sheets, for example using embossing or debossing rollers. This may enhance the structural integrity of the aerosol generating article.

In embodiments in which the inductively heatable susceptor comprises a continuous sheet of susceptor material, the method may further comprise perforating the aerosol generating sheets and the inductively heatable susceptor sheet positioned therebetween. The step of perforating the aerosol generating sheets and the inductively heatable susceptor sheet creates perforations which extend fully through the aerosol generating article. As noted above, the perforations facilitate air flow through the aerosol generating article during use in an aerosol generating device and may improve heating efficiency due to the skin effect. The perforations allow the porosity, and hence the air permeability, of the resultant aerosol generating article to be carefully controlled and optimised.

The step of perforating the aerosol generating sheets and the inductively heatable susceptor sheet positioned therebetween may be performed mechanically (for example by perforating rollers or by the abovementioned embossing rollers or debossing rollers), electrostatically or by laser.

In embodiments in which the inductively heatable susceptor comprises a continuous sheet of susceptor material, the method may comprise deforming or stretching an edge region of at least one of the aerosol generating sheets to cover an edge region of the inductively heatable susceptor sheet.

The deforming or stretching step may be conducted at the same time as the cutting or perforating step. In particular, the step of cutting the aerosol generating sheets and the inductively heatable susceptor sheet positioned therebetween may comprise the step of deforming edge regions of the aerosol generating sheets to cover corresponding edge regions of the inductively heatable susceptor sheet. The step of deforming the edge regions may conduct stretching of both of the aerosol generating sheets. A cutting tool comprising first and second cutting members may be used to perform the cutting step. An edge of each cutting member may be a pointed edge which has a summit at a midpoint of the edge. The first cutting member may cut the aerosol generating sheets and the inductively heatable susceptor sheet from one side and the second cutting member may cut the aerosol generating sheets and the inductively heatable susceptor sheet from an opposite side at the same time and at the same position along the sheets so that cut edge regions of the aerosol generating sheets cover corresponding edge regions of the inductively heatable susceptor sheet.

The cutting tool or both cutting members comprising curved sharp cutting edges may be used to perform the cutting step so that cut edge regions of the aerosol generating sheets more reliably cover corresponding edge regions of the inductively heatable susceptor sheet. The cutting tool or both cutting members may comprise the curved sharp cutting edges on both sides so that both cut edge regions of the aerosol generating sheets cover corresponding edge regions of the inductively heatable susceptor sheet. This process can be reliably performed if the thickness of the aerosol generating sheets is greater than the thickness of the inductively heatable susceptor sheet.

The inductively heatable susceptor sheet is thereby completely enclosed by the aerosol generating material of the aerosol generating sheets. One advantage of this approach is that it may improve heating efficiency. Another advantage of this approach is that it may extend the shelf-life of the inductively heatable susceptor sheet by virtue of the fact that the aerosol generating sheets and optional adhesive may form a protective enclosure around the inductively heatable susceptor sheet (e.g. comprising iron), thereby preventing oxidation of the inductively heatable susceptor.

The step of perforating the aerosol generating sheets and the inductively heatable susceptor sheet positioned therebetween may comprise the step of deforming edge regions of the aerosol generating sheets to cover corresponding edge regions of the inductively heatable susceptor sheet. In this case, the mechanical perforating tool (e.g. perforating rollers, embossing rollers or debossing rollers) or the punch tool comprises the pointed edge and/or the curved sharp edges.

BRIEF DESCRIPTION OF THE DRAWINGS

FIGS. 6b and 6c are diagrammatic illustrations of one example of a cutter used in the apparatus and method of FIG. 6a;

DETAILED DESCRIPTION OF EMBODIMENTS

Embodiments of the present disclosure will now be described by way of example only and with reference to the accompanying drawings.

Figure 1:
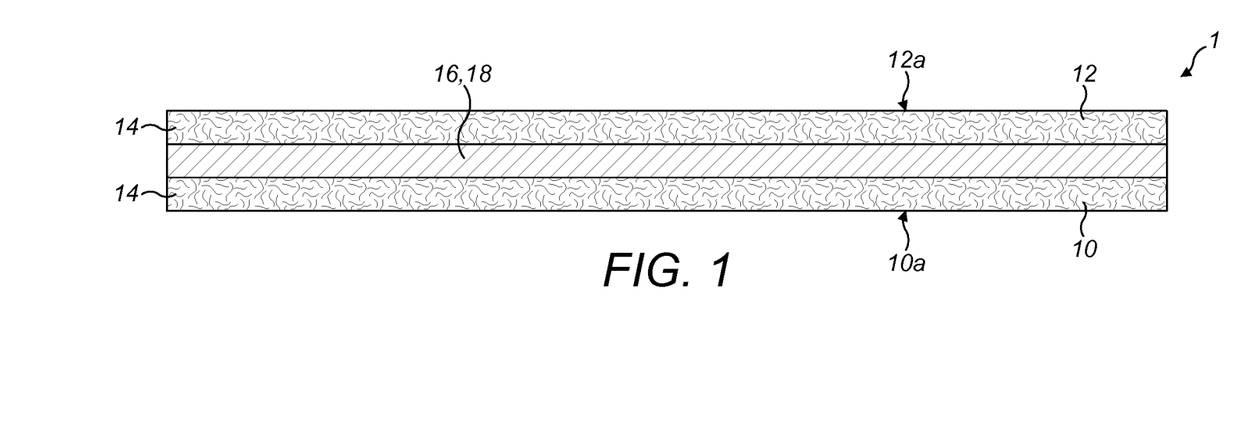
FIG. 1 is a diagrammatic cross-sectional view of a first example of an aerosol generating article.

Referring initially to FIG. 1, there is shown a first example of an aerosol generating article 1 for use with an aerosol generating device, an example of which will be described later in this specification. The aerosol generating article 1 is elongate and has a sheet-type form which, amongst other things, facilitates handling of the article 1 by a user and insertion of the article 1 into a heating compartment of an aerosol generating device.

The aerosol generating article 1 comprises first and second aerosol generating sheets 10, 12 each comprising aerosol generating material 14. The aerosol generating material 14 is typically a solid or semi-solid material. Examples of suitable aerosol generating solids include powder, shreds, strands, porous material or foam material. The aerosol generating material typically comprises plant derived material and, in particular, comprises tobacco. The aerosol generating material 14 may alternatively comprise an aerosol generating liquid impregnated into or absorbed by a liquid absorbent material forming the aerosol generating sheets 10, 12.

The aerosol generating article 1 comprises an inductively heatable susceptor 16 having a thickness which is preferably less than the thickness of the aerosol generating sheets 10, 12. The inductively heatable susceptor 16 is positioned between the first and second aerosol generating sheets 10, 12 and is inductively heatable in the presence of a time varying electromagnetic field. In the illustrated first example, the inductively heatable susceptor 16 comprises a sheet of susceptor material 18 which separates, and is adhered to, the first and second aerosol generating sheets 10, 12 by a substantially non-electrically conductive and non-magnetically permeable adhesive.

When a time varying electromagnetic field is applied in the vicinity of the inductively heatable susceptor 16 during use of the article 1 in an aerosol generating device, heat is generated in the inductively heatable susceptor 16 due to eddy currents and magnetic hysteresis losses and the heat is transferred from the inductively heatable susceptor 16 to the adjacent first and second aerosol generating sheets 10, 12 to heat the aerosol generating material 14 without burning it and to thereby generate an aerosol for inhalation by a user. The inductively heatable susceptor sheet 18 is in contact over its entire surfaces with the adjacent first and second aerosol generating sheets 10, 12, thus enabling heat to be transferred directly, and therefore efficiently, from the inductively heatable susceptor sheet 18 to the aerosol generating material 14.

The aerosol generating material 14 of the first and second aerosol generating sheets 10, 12 comprises at least one aerosol-former such as glycerine or propylene glycol.

Typically, the aerosol generating material 14 may comprise an aerosol-former content of between approximately 5% and approximately 50% on a dry weight basis. Upon heating due to heat transfer from the inductively heatable susceptor sheet 18, the aerosol generating material 14 of both the first and second aerosol generating sheets 10, 12 releases volatile compounds possibly including nicotine or flavour compounds such as tobacco flavouring. Each of the aerosol generating sheets 10, 12 has an exposed surface 10a, 12a thus ensuring that the generated aerosol can be easily released.

Figure 2:
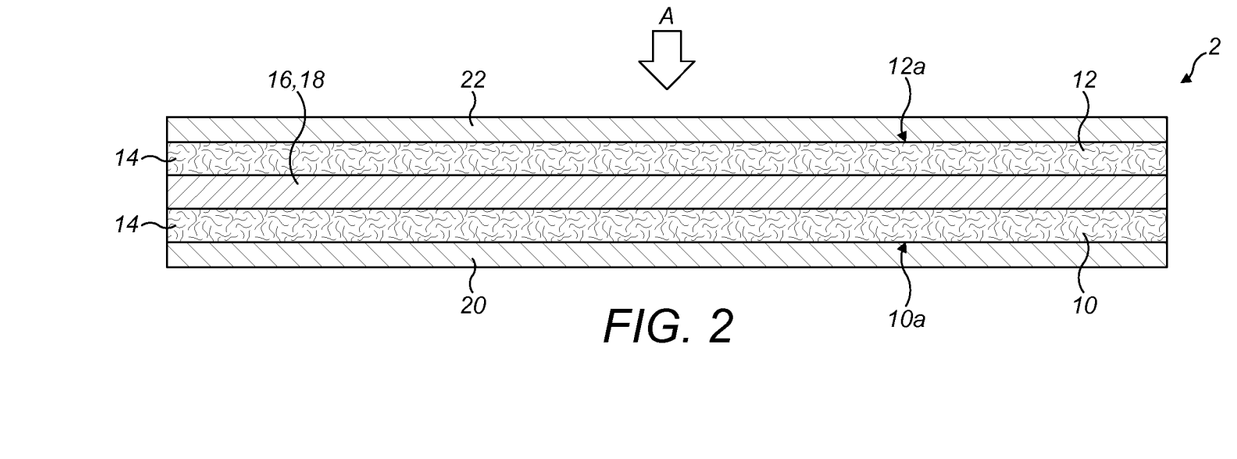
FIG. 2 is a diagrammatic cross-sectional view of a second example of an aerosol generating article similar to the first example shown in FIG. 1.
Figure 3:
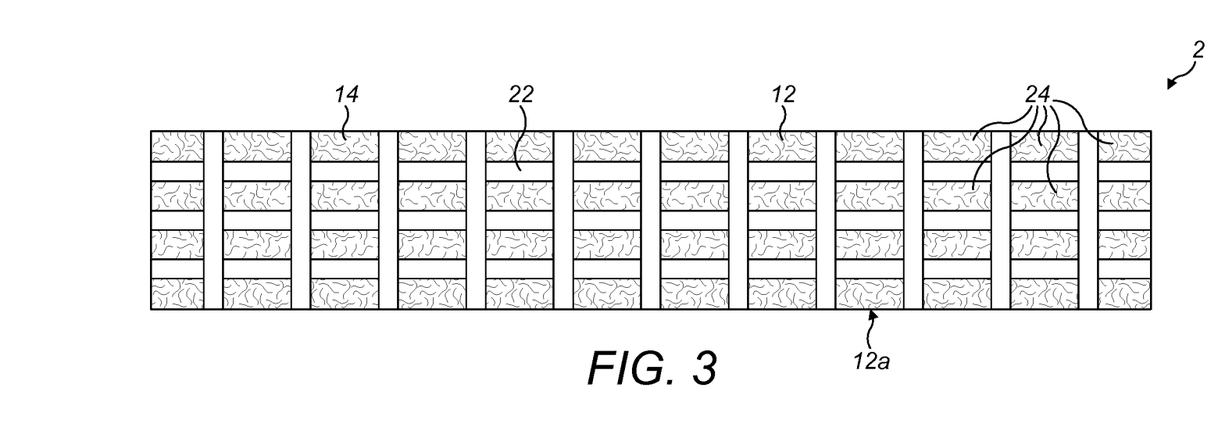
FIG. 3 is a diagrammatic view of the second example of the aerosol generating article in the direction of arrow A in FIG. 2.

Referring now to FIGS. 2 and 3, there is shown a second example of an aerosol generating article 2 which is similar to the aerosol generating article 1 illustrated in FIG. 1 and in which corresponding elements are designated using the same reference numerals.

The aerosol generating article 2 is identical to the aerosol generating article 1 illustrated in FIG. 1 in all respects and in addition comprises a further layer or sheet 20, 22 covering each of the first and second aerosol generating sheets 10, 12. The further layer or sheet 20, 22 comprises a material which differs from the aerosol generating material 14 and the material of the inductively heatable susceptor sheet 18 and is provided to facilitate handling of the aerosol generating article 2 by a user. The further layer or sheet 20, 22 typically comprises a material which is non-electrically conductive and non-magnetically permeable so that it is not heated in the presence of a time-varying electromagnetic field during use of the article 2 in an aerosol generating device. In typical embodiments, the further layer or sheet 20, 22 comprises paper.

The further layer or sheet 20, 22 is air-permeable to facilitate the release of generated aerosol from the first and second aerosol generating sheets 10, 12. As best seen in FIG. 3, the further layer or sheet 20, 22 comprises a plurality of openings 24 across its surface which expose the surfaces 10a, 10b of the aerosol generating sheets 10, 12 and provide the further layer or sheet 20, 22 with the desired level of air permeability.

Figure 4:
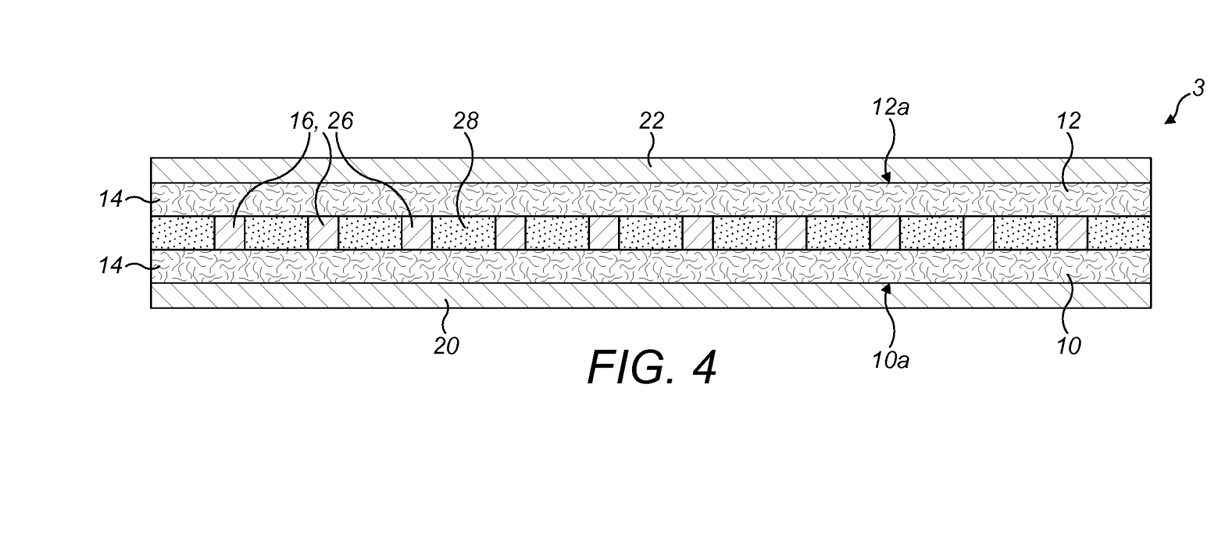
FIG. 4 is a diagrammatic cross-sectional view of a third example of an aerosol generating article similar to the second example shown in FIGS. 2 and 3.

Referring now to FIG. 4, there is shown a diagrammatic cross-sectional view of a third example of an aerosol generating article 3 which is similar to the aerosol generating article 2 illustrated in FIGS. 2 and 3 and in which corresponding elements are designated using the same reference numerals.

The aerosol generating article 3 is identical to the aerosol generating article 2 illustrated in FIGS. 2 and 3 in all respects except that the inductively heatable susceptor 16 comprises a plurality of strips or particles of susceptor material 26 positioned in an adhesive layer 28 between the first and second aerosol generating sheets 10, 12. It will be seen in FIG. 4 that the adhesive layer 28 contacts the first and second aerosol generating sheets 10, 12 and thereby securely adheres them to each other.

Figure 5A:
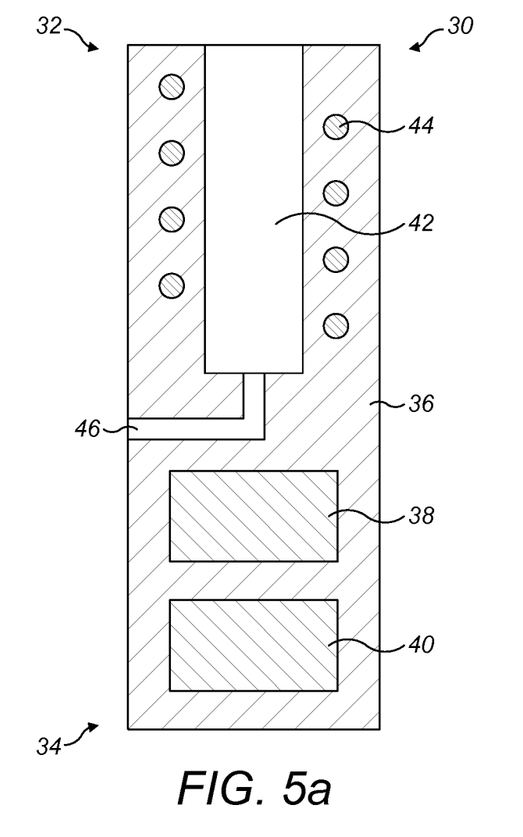
FIGS. 5a and 5b are diagrammatic cross-sectional and top views respectively of an aerosol generating device for use with aerosol generating articles according to the present disclosure.
Figure 5B:
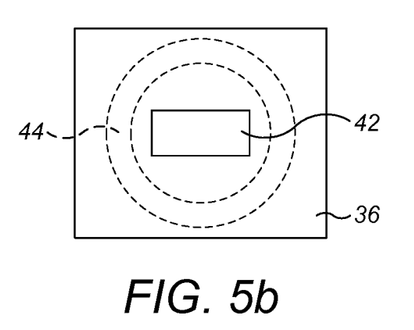
Figure 5C:
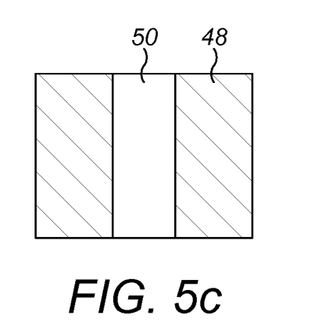
FIG. 5c is a diagrammatic cross-sectional view of a mouthpiece for use with the aerosol generating device of FIGS. 5a and 5b.

Referring now to FIGS. 5a to 5c, there is shown an example of an aerosol generating device 30 for use with the aerosol generating articles 1, 2, 3 described above for generating an aerosol to be inhaled.

The aerosol generating device 30 has a proximal end 32 and a distal end 34 and comprises a device body 36 which includes a power source 38 and a controller 40 which may be configured to operate at high frequency. The power source 38 typically comprises one or more batteries which could, for example, be inductively rechargeable.

The aerosol generating device 30 comprises an aerosol generating space 42, for example in the form of a heating compartment, accessible from the proximal end 32 of the aerosol generating device 30. The aerosol generating space 42 has a rectangular cross-section as best seen in FIG. 5b and is arranged to receive a correspondingly shaped sheet-type aerosol generating article 1, 2, 3 as described above.

The aerosol generating device 30 comprises a helical induction coil 44 which has a circular cross-section and which extends around the aerosol generating space 42. The induction coil 44 can be energised by the power source 38 and controller 40. The controller 40 includes, amongst other electronic components, an inverter which is arranged to convert a direct current from the power source 38 into an alternating high-frequency current for the induction coil 44.

The aerosol generating device 30 includes an air inlet 46 in the device body 36 which allows ambient air to flow into the aerosol generating space 42. The aerosol generating device 30 also includes a mouthpiece 48 having an air outlet 50. The mouthpiece 48 is removably mountable on the device body 36 at the proximal end 32 to allow access to the aerosol generating space 42 for the purposes of inserting or removing a sheet-type aerosol generating article 1, 2, 3 as described above.

As will be understood by one of ordinary skill in the art, when the induction coil 44 is energised during use of the aerosol generating device 30, an alternating and time-varying electromagnetic field is produced. This couples with the inductively heatable susceptor 16 of an aerosol generating article 1, 2, 3 positioned in the aerosol generating space 42 and generates eddy currents and/or magnetic hysteresis losses in the inductively heatable susceptor 16 causing it to heat up. The heat is then transferred from the inductively heatable susceptor 16 to the aerosol generating material 14 of the first and second aerosol generating sheets 10, 12, for example by conduction, radiation and convection, to heat the aerosol generating material 14 and thereby generate an aerosol.

The aerosolisation of the aerosol generating material 14 is facilitated by the addition of air from the surrounding environment through the air inlet 46. The aerosol generated by heating the aerosol generating material 14 in the first and second aerosol generating sheets 10, 12 exits the aerosol generating space 42 through the air outlet 50 in the mouthpiece 48 where it can be inhaled by a user of the device 30. The flow of air through the aerosol generating space 42, i.e. from the air inlet 46, through the aerosol generating space 42 and out of the air outlet 50, can be aided by negative pressure created by a user drawing air from the air outlet 50 side of the device 30.

Examples of apparatus and methods for manufacturing aerosol generating articles in accordance with the present disclosure will now be described with reference to FIGS. 6 to 10.

Figure 6A:
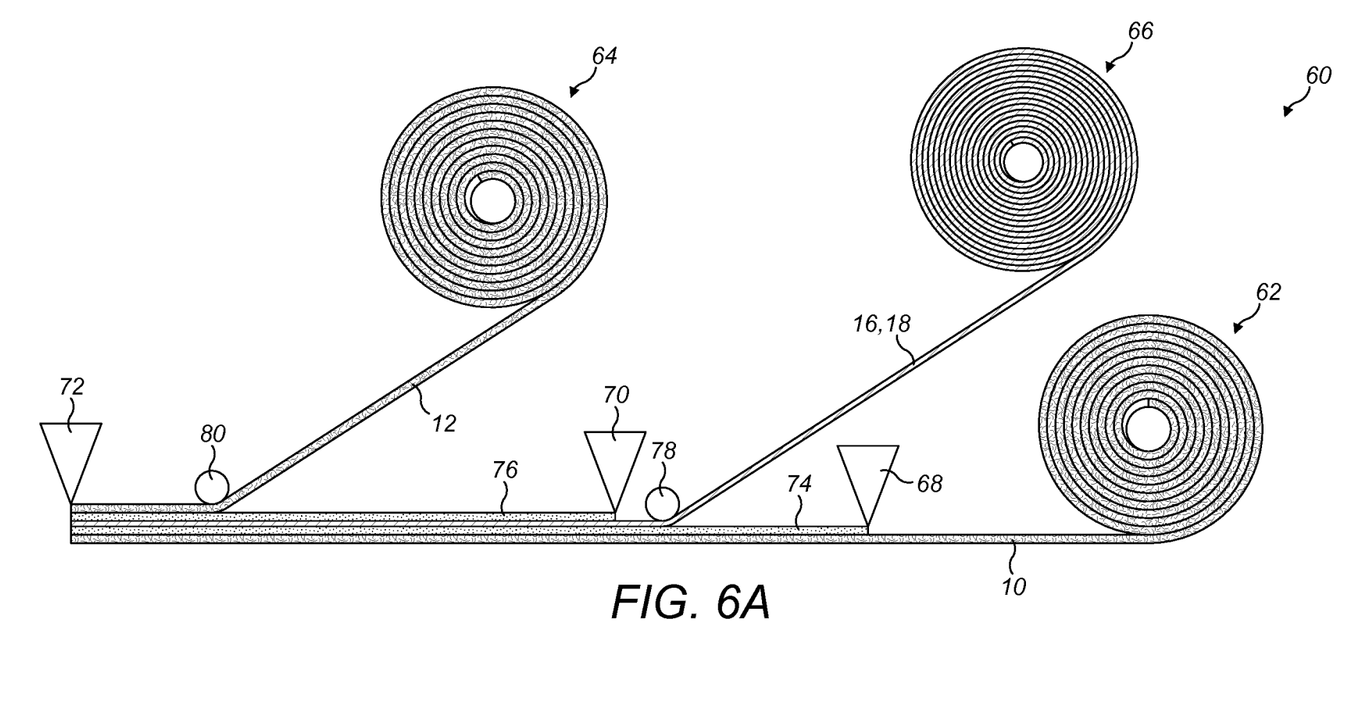
FIG. 6a is a diagrammatic view of an apparatus and method for manufacturing the first example of the aerosol generating article shown in FIG. 1.
Figure 6B:
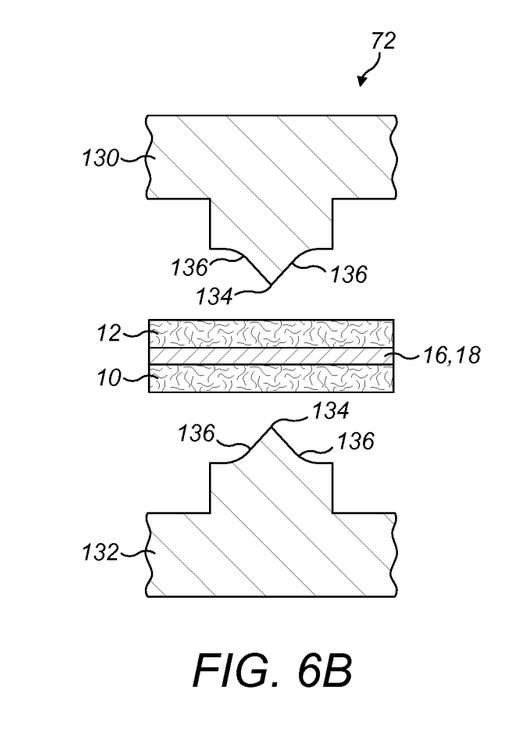
Figure 6C:
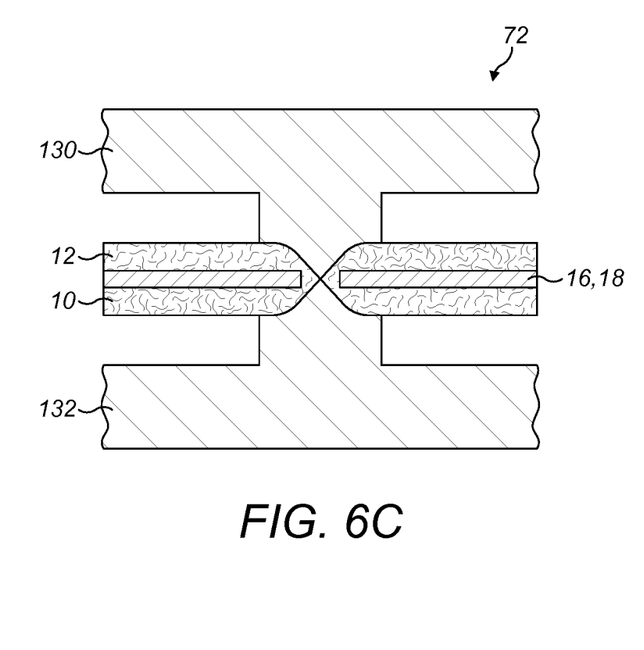
Figure 7:
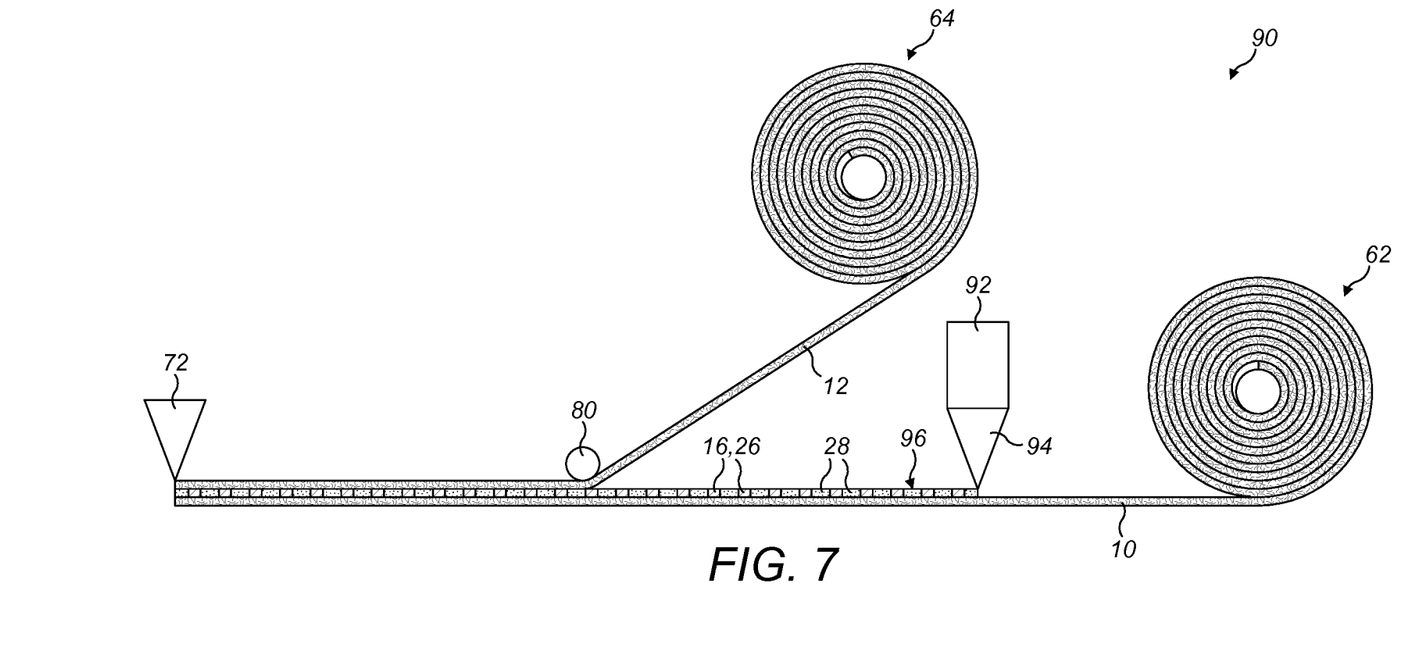
FIG. 7 is a diagrammatic view of an apparatus and method for manufacturing the third example of the aerosol generating article shown in FIG. 4.
Figure 8:
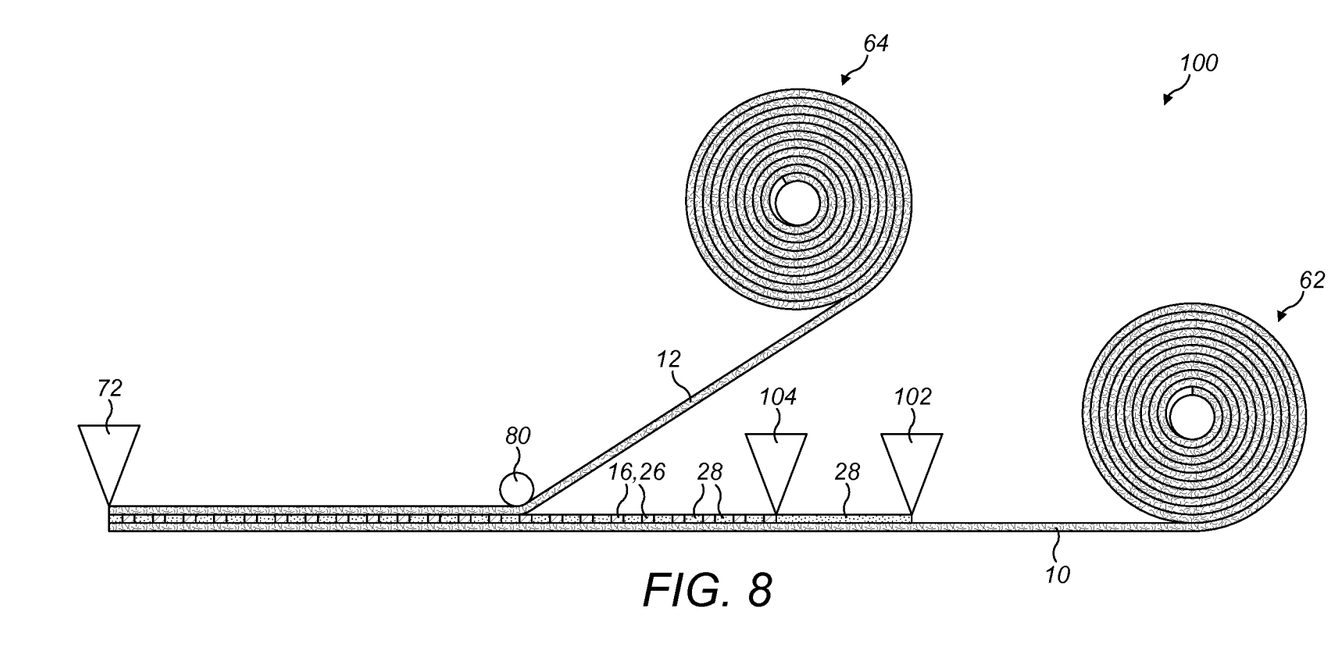
FIG. 8 is a diagrammatic view of an alternative apparatus and method for manufacturing the third example of the aerosol generating article shown in FIG. 4.
Figure 9:
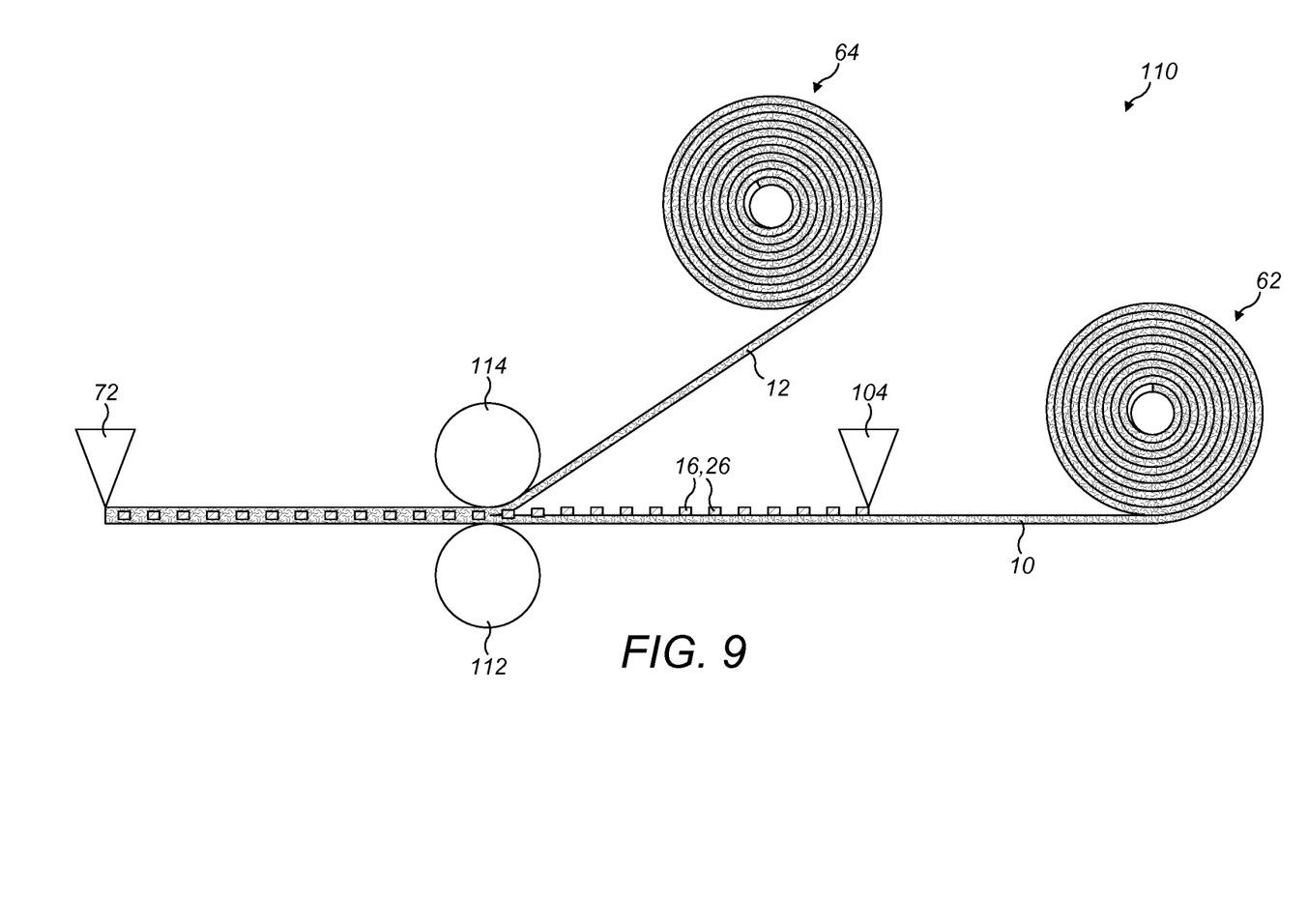
FIG. 9 is a diagrammatic view of an apparatus and method for manufacturing a fourth example of an aerosol generating article.
Figure 10:
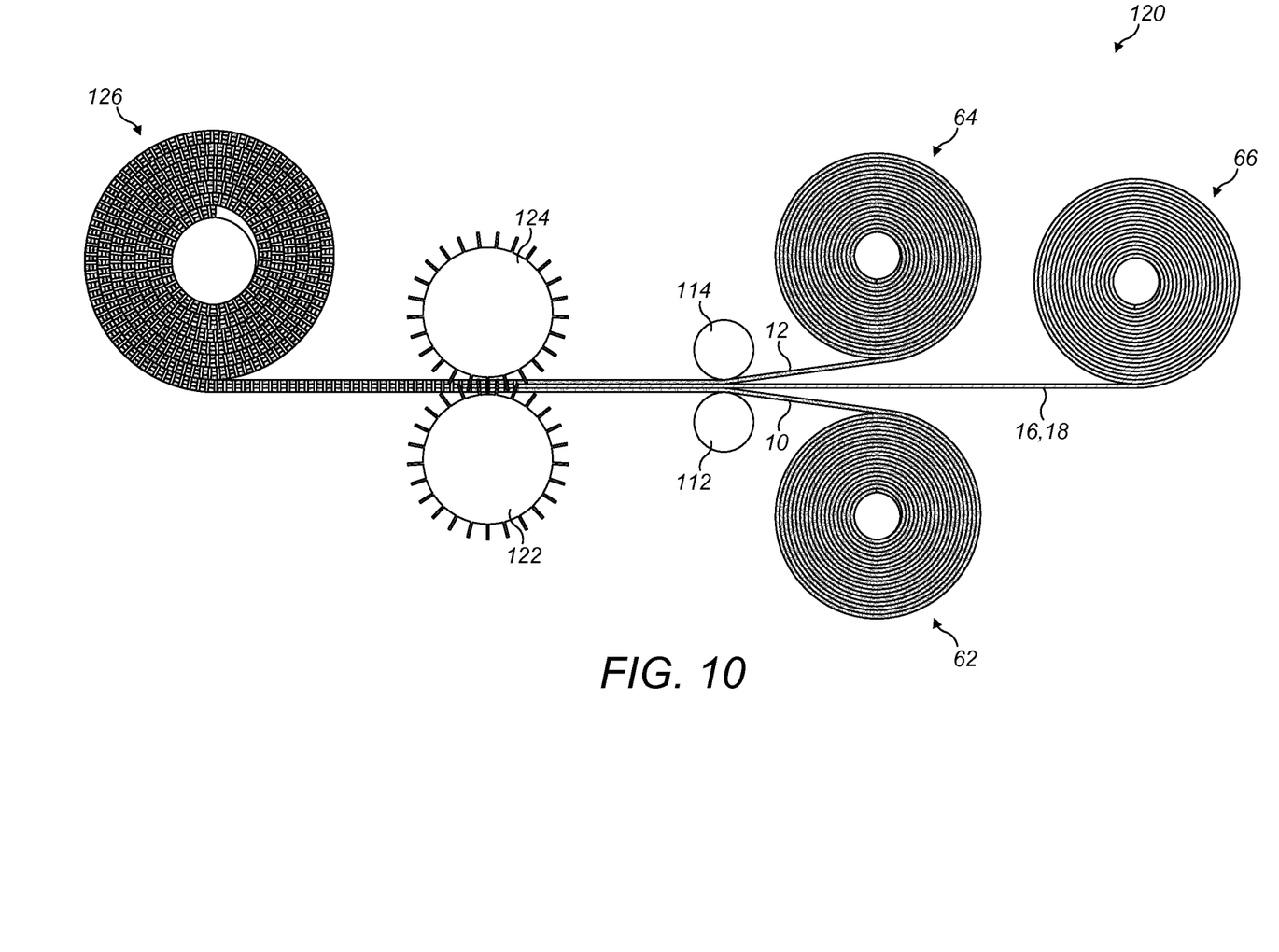
FIG. 10 is a diagrammatic view of an apparatus and method for manufacturing a fifth example of an aerosol generating article.

Referring initially to FIG. 6a, there is shown a diagrammatic illustration of an apparatus 60 and method for manufacturing the first example of the aerosol generating article 1 described above with reference to FIG. 1.

The apparatus 60 comprises first and second supply reels 62, 64 each carrying first and second aerosol generating sheets 10, 12 in continuous sheet form and a third supply reel 66 carrying an inductively heatable susceptor 16 in the form of a continuous sheet 18. The apparatus 60 also comprises first and second adhesive applicators 68, 70, such as nozzles, and a cutter 72.

The first aerosol generating sheet 10 is supplied from the first supply reel 62 and a first adhesive layer 74 is applied to a surface of the first aerosol generating sheet 10 by the first adhesive applicator 68. The continuous sheet 18 of inductively heatable susceptor 16 is supplied from the third supply reel 66 and is pressed into contact with the first adhesive layer 74 by a press roller 78 before a second adhesive layer 76 is applied to a surface of the continuous sheet 18 of inductively heatable susceptor 16 by the second adhesive applicator 70. The second aerosol generating sheet 12 is then supplied from the second supply reel 64 and is pressed into contact with the second adhesive layer 76 by a press roller 80 to produce a continuous sheet-type article. Finally, the continuous sheet-type article is cut at appropriate positions by the cutter 72 into predetermined lengths to form multiple sheet-type aerosol generating articles 1. It will be understood that this type of method is suitable for the mass production of aerosol generating articles 1.

FIGS. 6*b* and 6*c* illustrate an example of the cutter 72 which comprises first and second cutting members 130, 132 (note that the first and second adhesive layers 74, 76 are omitted from these figures for clarity). The first and second cutting members 130, 132 each have a sharp cutting edge 134 and concave curved portions 136 which extend away from the cutting edge 134.

In order to cut the continuous sheet-type article at appropriate positions into predetermined lengths to form multiple sheet-type aerosol generating articles 1, the first and second cutting members 130, 132 are moved towards each other to bring the cutting edges 134 into contact as shown in FIG. 6*c*. During movement of the first and second cutting members 130, 132 towards each other, it will be seen from FIG. 6*c* that the edge regions of the aerosol generating sheets 10, 12 are deformed, for example stretched, by the concave curved portions 136 of the first and second cutting members 130, 132 to cover and enclose corresponding edge regions of the inductively heatable susceptor sheet 18. The deformation of the edge regions of the aerosol generating sheets 10, 12 is facilitated because the thickness of the aerosol generating sheets 10, 12 is greater than the thickness of the inductively heatable susceptor sheet 18.

Referring now to FIG. 7, there is shown a diagrammatic illustration of an apparatus 90 and method for manufacturing the third example of the aerosol generating article 3 described above with reference to FIG. 4.

The apparatus 90 comprises first and second supply reels 62, 64, a press roller 80 and a cutter 72 as described above. The apparatus 90 additionally comprises a mixer 92 for mixing together an inductively heatable susceptor 16, for example comprising a plurality of particles of susceptor material 26, and an adhesive 28 to form an adhesive/particulate mixture 96 which is stored in a hopper 94.

The first aerosol generating sheet 10 is supplied from the first supply reel 62 and the adhesive/particulate mixture 96 is applied to a surface of the first aerosol generating sheet 10 by an applicator associated with the hopper 94. The second aerosol generating sheet 12 is then supplied from the second supply reel 64 and is pressed into contact with the adhesive/particulate mixture 96 by the press roller 80 to produce a continuous sheet-type article in which the first and second aerosol generating sheets 10, 12 are secured together by the adhesive layer 28. Finally, the continuous sheet-type article is cut at appropriate positions by the cutter 72 into predetermined lengths to form multiple sheet-type aerosol generating articles 3. This type of method is suitable for the mass production of aerosol generating articles 3 and is particularly convenient if the particles of susceptor material 26 have relatively small dimensions.

Referring now to FIG. 8, there is shown a diagrammatic illustration of an alternative apparatus 100 and method for manufacturing the third example of the aerosol generating article 3 described above with reference to FIG. 4.

The apparatus 100 comprises first and second supply reels 62, 64, a press roller 80 and a cutter 72 as described above. The apparatus 90 additionally comprises an adhesive applicator 102 and a hopper 104 containing a supply of particles of susceptor material 26.

The first aerosol generating sheet 10 is supplied from the first supply reel 62 and an adhesive layer 28 is applied to a surface of the first aerosol generating sheet 10 by the adhesive applicator 102. The particles of susceptor material 26 are then supplied from the hopper 104 onto the previously deposited adhesive layer 28 before the second aerosol generating sheet 12 is then supplied from the second supply reel 64 and is pressed into contact with the adhesive layer 28 containing the particles of susceptor material 26 by the press roller 80 to produce a continuous sheet-type article. Finally, the continuous sheet-type article is cut at appropriate positions by the cutter 72 into predetermined lengths to form multiple sheet-type aerosol generating articles 3. It will again be understood that this type of method is suitable for the mass production of aerosol generating articles 3 and allows carefully controlled deposition of the particles of susceptor material 26 onto the previously deposited adhesive layer 28, for example at predetermined positions or in a predetermined pattern.

Referring now to FIG. 9, there is shown a diagrammatic illustration of an apparatus 110 and method for manufacturing a fourth example of an aerosol generating article.

The apparatus 110 comprises first and second supply reels 62, 64, a hopper 104 containing a supply of particles of susceptor material 26, first and second cooperating nip rollers 112, 114 and a cutter 72.

The first aerosol generating sheet 10 is supplied from the first supply reel 62 and particles of susceptor material 26 are then deposited from the hopper 104 onto a surface of the first aerosol generating sheet 10. The second aerosol generating sheet 12 is then supplied from the second supply reel 64 and the first and second aerosol generating sheets 10, 12 with the particles of susceptor material 26 positioned therebetween are pressed firmly together by the cooperating nip rollers 112, 114. The pressure applied by the nip rollers 112, 114 is sufficient to bond the first and second aerosol generating sheets 10, 12 together with the particles of induction heatable susceptor 26 positioned therebetween. Finally, the continuous sheet-type article is cut at appropriate positions by the cutter 72 into predetermined lengths to form multiple sheet-type aerosol generating articles. It will again be understood that this type of method is suitable for the mass production of aerosol generating articles and advantageously allows the articles to be manufactured without the use of an adhesive.

Referring now to FIG. 10, there is shown a diagrammatic illustration of an apparatus 120 and method for manufacturing a fifth example of an aerosol generating article which is similar to the first example of the aerosol generating article 1 illustrated in FIG. 1.

The apparatus 120 comprises first and second supply reels 62, 64 each carrying first and second aerosol generating sheets 10, 12 in continuous sheet form and a third supply reel 66 carrying an inductively heatable susceptor 16 in the form of a continuous sheet 18. The apparatus 120 also comprises first and second cooperating nip rollers 112, 114, first and second cooperating perforating rollers 122, 124 and a take up bobbin 126.

The first and second aerosol generating sheets 10, 12 are supplied from the first and second supply reels 62, 64 and are positioned on opposite sides of the inductively heatable susceptor sheet 18 supplied from the third supply reel 66. The first and second aerosol generating sheets 10, 12 with the inductively heatable susceptor sheet 18 positioned therebetween are then pressed firmly together as they are fed through the cooperating nip rollers 112, 114. The pressure applied by the nip rollers 112, 114 is sufficient to secure together the first and second aerosol generating sheets 10, 12 and the inductively heatable susceptor sheet 18 to form a sandwich of the sheets 10, 12, 18. The nip rollers 112, 114 can also be heated if desired so that the sheets 10, 12, 18 are pressed together at an elevated temperature.

The continuous sandwich formed by the sheets 10, 12, 18 is then passed through the perforating rollers 122, 124. The perforating rollers 122, 124 include formations which perforate the aerosol generating sheets 10, 12 and the inductively heatable susceptor sheet 18 positioned therebetween so that the sandwich formed by the sheets 10, 12, 18 includes perforations which extend fully through the sheets 10, 12, 18. The size and distribution of the perforations can be carefully controlled by appropriate design of the formations on the perforating rollers 122, 124 to enable the air permeability of the sheets 10, 12, 18, and of the resultant aerosol generating articles, to be likewise carefully controlled and optimised. The formations on the perforating rollers 122, 124 can also be designed and configured so that when the continuous sandwich formed by the sheets 10, 12, 18 is passed through the perforating rollers 122, 124, the edge regions (including around each of the perforations) of the aerosol generating sheets 10, 12 are deformed, for example stretched, to cover and enclose corresponding edge regions of the inductively heatable susceptor sheet 18.

The continuous sandwich formed by the perforated sheets 10, 12, 18 is finally wound onto the take up bobbin 126. The bobbinized sandwich formed by the perforated sheets 10, 12, 18 can subjected to further processing operations if desired and cut at appropriate positions to form aerosol generating articles of a desired size.

Although exemplary embodiments have been described in the preceding paragraphs, it should be understood that various modifications may be made to those embodiments without departing from the scope of the appended claims. Thus, the breadth and scope of the claims should not be limited to the above-described exemplary embodiments.

Any combination of the above-described features in all possible variations thereof is encompassed by the present disclosure unless otherwise indicated herein or otherwise clearly contradicted by context.

Unless the context clearly requires otherwise, throughout the description and the claims, the words "comprise", "comprising", and the like, are to be construed in an inclusive as opposed to an exclusive or exhaustive sense; that is to say, in the sense of "including, but not limited to".

The invention claimed is:

1. An aerosol generating article comprising:
   at least two aerosol generating sheets each comprising aerosol generating material; and
   an inductively heatable susceptor;
   wherein the inductively heatable susceptor is positioned between two of the at least two aerosol generating sheets and each of the at least two aerosol generating sheets has an exposed surface, and
   further including perforations which extend through the article.

2. The aerosol generating article according to claim 1, wherein the inductively heatable susceptor comprises a sheet of susceptor material separating two of the at least two aerosol generating sheets.

3. The aerosol generating article according to claim 2, wherein an edge region of the sheet of susceptor material is covered by a stretched or deformed edge region of at least one of the at least two aerosol generating sheets.

4. An aerosol generating article comprising:
   at least two aerosol generating sheets each comprising aerosol generating material; and
   an inductively heatable susceptor;
   wherein the inductively heatable susceptor is positioned between two of the at least two aerosol generating sheets and each of the at least two aerosol generating sheets has an exposed surface, and
   wherein the inductively heatable susceptor comprises a plurality of strips of susceptor material.

5. The aerosol generating article according to claim 1, wherein the inductively heatable susceptor comprises a particulate susceptor material.

6. The aerosol generating article according to claim 1, further comprising a further layer or sheet covering each of the at least two aerosol generating sheets, the further layer or sheet comprising a material which differs from the aerosol generating material and a material of the inductively heatable susceptor.

7. The aerosol generating article according to claim 1, wherein the at least two aerosol generating sheets are adhered to each other by an adhesive.

8. The aerosol generating article according to claim 7, wherein a layer of the adhesive is disposed between two of the at least two aerosol generating sheets, and the inductively heatable susceptor is provided in the adhesive layer.

9. A method for manufacturing an aerosol generating article comprising:
   (i) positioning an inductively heatable susceptor between two aerosol generating sheets each comprising aerosol generating material, each of the aerosol generating sheets having an exposed surface; and
   (ii) perforating the two aerosol generating sheets and the susceptor positioned therebetween, forming perforations that extend through the article.

10. The method according to claim 9, wherein the two aerosol generating sheets are continuous sheets and the method further comprises:
    (iii) cutting the continuous sheets with the susceptor positioned therebetween.

11. The method according to claim 10, wherein the inductively heatable susceptor is a continuous susceptor and step (iii) comprises simultaneously cutting the continuous sheets and the continuous susceptor positioned therebetween.

12. The method according to claim 9, wherein step (i) comprises positioning the inductively heatable susceptor on a first one of said two aerosol generating sheets and positioning a second one of said two aerosol generating sheets on the susceptor.

13. The method according to claim 9, wherein step (i) comprises:
    mixing the inductively heatable susceptor with an adhesive to form a mixture; and
    positioning the mixture on a first one of said two aerosol generating sheets.

14. The method according to claim 9, wherein step (i) comprises:
    positioning an adhesive on a first one of said two aerosol generating sheets; and
    positioning the inductively heatable susceptor on the adhesive.

15. The method according to claim 9, wherein the method further comprises pressing the two aerosol generating sheets and the inductively heatable susceptor positioned therebetween to thereby bond the two aerosol generating sheets.

16. The method according to claim 9, wherein the inductively heatable susceptor comprises a continuous sheet of susceptor material.

17. The method according to claim 9, wherein the inductively heatable susceptor comprises a continuous sheet of susceptor material and the method comprises deforming or stretching an edge region of at least one of the two aerosol generating sheets to cover an edge region of the sheet of susceptor material.

18. The aerosol generating article according to claim 1, wherein the at least two aerosol generating sheets are adhered to the inductively heatable susceptor.

* * * * *